United States Patent
Arima

(10) Patent No.: US 10,405,819 B2
(45) Date of Patent: Sep. 10, 2019

(54) IMAGING CONTROL APPARATUS, IMAGING CONTROL SYSTEM, AND IMAGING CONTROL METHOD

(71) Applicant: CANON KABUSHIKI KAISHA, Tokyo (JP)

(72) Inventor: Keisuke Arima, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 553 days.

(21) Appl. No.: 14/668,745

(22) Filed: Mar. 25, 2015

(65) Prior Publication Data

US 2015/0272703 A1    Oct. 1, 2015

(30) Foreign Application Priority Data

Mar. 27, 2014  (JP) ................. 2014-066246

(51) Int. Cl.
*A61B 19/00* (2006.01)
*A61B 6/00* (2006.01)
*G06F 19/00* (2018.01)

(52) U.S. Cl.
CPC .............. *A61B 6/461* (2013.01); *A61B 6/465* (2013.01); *A61B 6/467* (2013.01); *A61B 6/548* (2013.01); *G06F 19/321* (2013.01); *A61B 6/563* (2013.01)

(58) Field of Classification Search
None
See application file for complete search history.

(56) References Cited

U.S. PATENT DOCUMENTS

| | | | | |
|---|---|---|---|---|
| 2003/0139665 A1* | 7/2003 | Takayama | .............. | G16H 40/40 600/407 |
| 2011/0208048 A1* | 8/2011 | Arima | .................... | A61B 6/465 600/436 |
| 2014/0180702 A1* | 6/2014 | Mansker | ................ | G06Q 50/22 705/2 |

FOREIGN PATENT DOCUMENTS

| JP | 2008-276288 A | 11/2008 |
|---|---|---|
| JP | 2012-187195 A | 10/2012 |
| JP | 2013-226258 A | 11/2013 |

\* cited by examiner

*Primary Examiner* — Tize Ma
(74) *Attorney, Agent, or Firm* — Canon U.S.A., Inc. IP Division

(57) ABSTRACT

If an X-ray imaging control apparatus receives a request to obtain a new examination order from an RIS 12 during a time period from a start of an examination to an end of the examination, the X-ray imaging control apparatus notifies the RIS 12 of rejection of acquisition of the new examination order, and does not receive the new examination order.

10 Claims, 14 Drawing Sheets

FIG. 2B

| EDITED ID | PATIENT ID | NAME OF PATIENT | SEX | DATE OF BIRTH | |
|---|---|---|---|---|---|
| O001 | P333 | SABURO AAA | MALE | NOVEMBER 11, 1981 | |
| O002 | P222 | JIRO BBB | MALE | FEBRUARY 2, 2002 | |
| O003 | P111 | TARO CCC | MALE | JANUARY 10, 2001 | |
| O004 | P777 | HANAKO DDD | FEMALE | JULY 7, 1977 | |
| O005 | P123 | ICHIRO EEE | MALE | MARCH 3, 2003 | |
| O006 | P444 | SHIRO FFF | MALE | APRIL 4, 1964 | EXAMINED |
| O007 | P555 | GORO GGG | MALE | MAY 5, 1955 | EXAMINED |
| O008 | P666 | ROKURO HHH | MALE | JUNE 6, 1976 | EXAMINED |

NAME OF PATIENT:
DATE OF BIRTH:
PATIENT ID:
AGE:
SEX: ○ MALE ○ FEMALE ○ OTHER
ENTER

NAME OF PATIENT:
PATIENT ID:
DATE OF BIRTH:
AGE:
SEX:

EXAMINATION ID:

ISSUE UPDATE INSTRUCTION — 108
INPUT IMAGING INFORMATION — 106
START EXAMINATION — 107

| PATIENT ID | NAME OF PATIENT | SEX | DATE OF BIRTH | |
|---|---|---|---|---|
| O001 | P333 | SABURO AAA | MALE | NOVEMBER 11, 1961 | |
| O002 | P222 | JIRO BBB | MALE | FEBRUARY 2, 2002 | |
| O003 | P111 | TARO CCC | MALE | JANUARY 10, 2001 | |
| O004 | P777 | HANAKO DDD | FEMALE | JULY 7, 1977 | |
| O005 | P123 | ICHIRO EEE | MALE | MARCH 3, 2003 | |
| O006 | P444 | SHIRO FFF | MALE | APRIL 4, 1964 | EXAMINED |
| O007 | P555 | GORO GGG | MALE | MAY 5, 1955 | EXAMINED |
| O008 | P666 | ROKURO HHH | MALE | JUNE 6, 1976 | EXAMINED |

NAME OF PATIENT:
DATE OF BIRTH: / /
PATIENT ID:
AGE:
SEX: ○MALE ○FEMALE ○OTHER
ENTER — 102

— 101
— 103

NAME OF PATIENT: TARO CCC
PATIENT ID: P111
DATE OF BIRTH: JANUARY 10, 2001
AGE: 8
SEX: MALE
— 104

EXAMINATION ID: O003
CHEST FRONT VIEW     SENSOR A — 109a
CHEST LATERAL VIEW   SENSOR A — 109b
— 105

ISSUE UPDATE INSTRUCTION — 108
INPUT IMAGING INFORMATION — 106
START EXAMINATION — 107

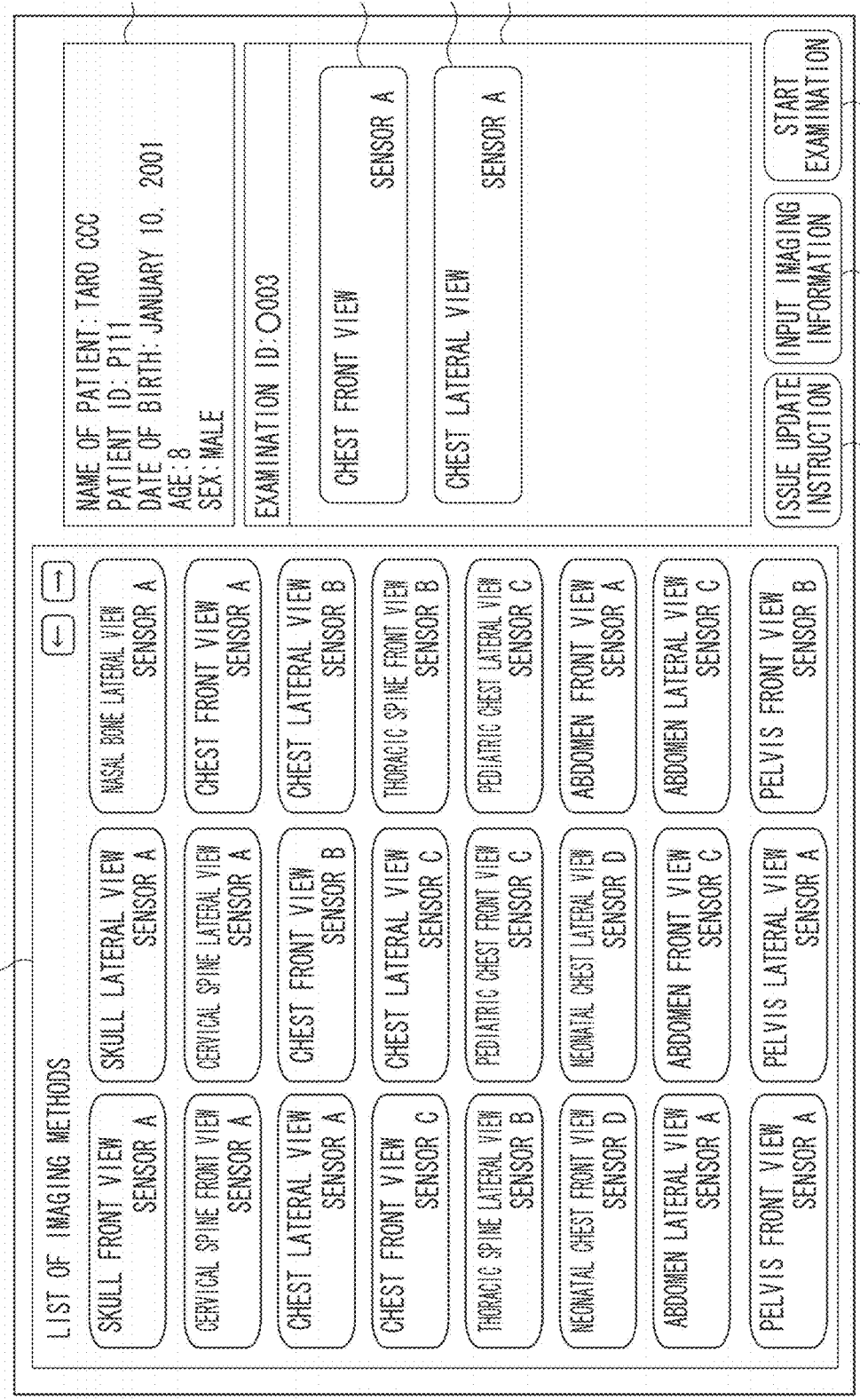

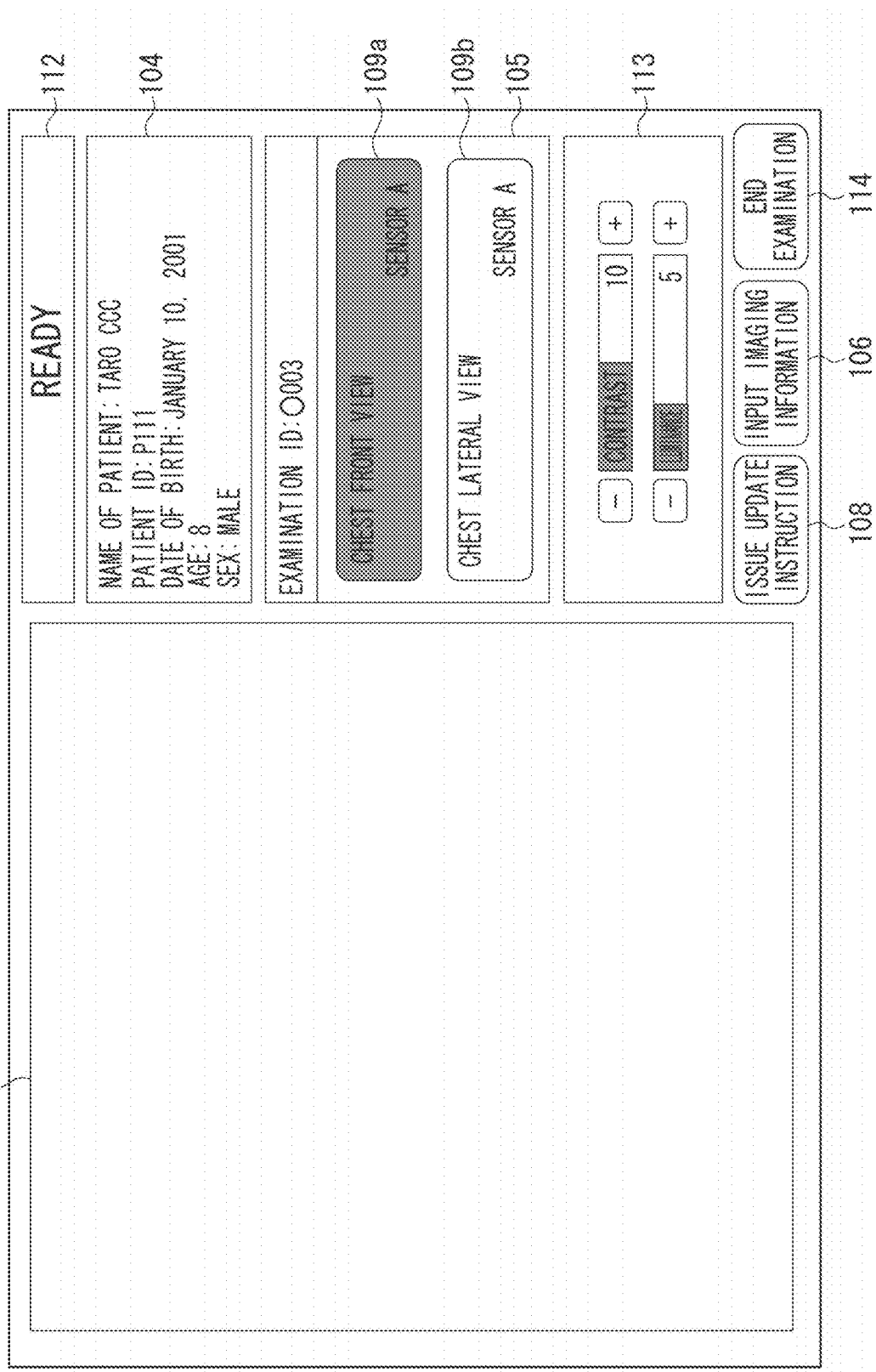

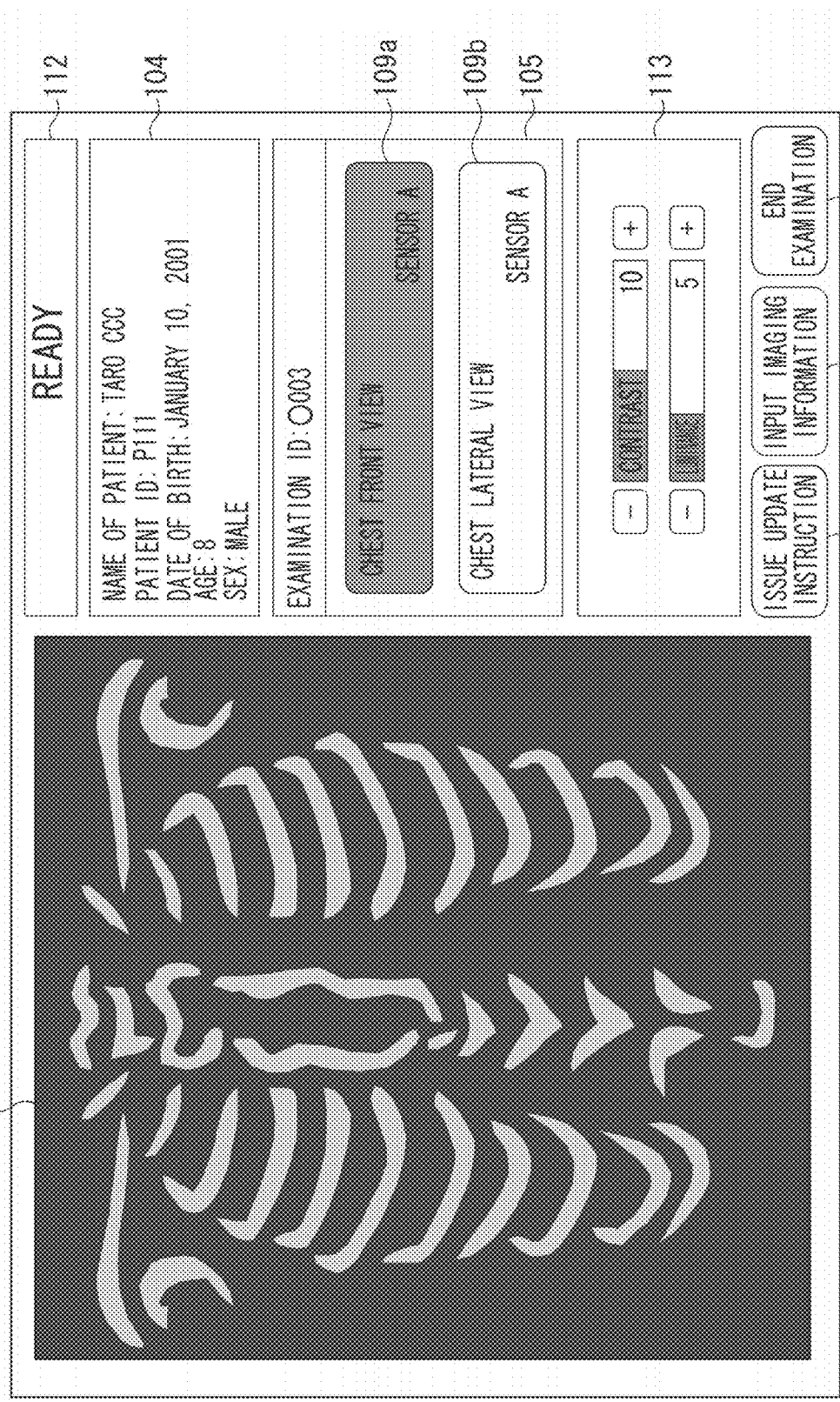

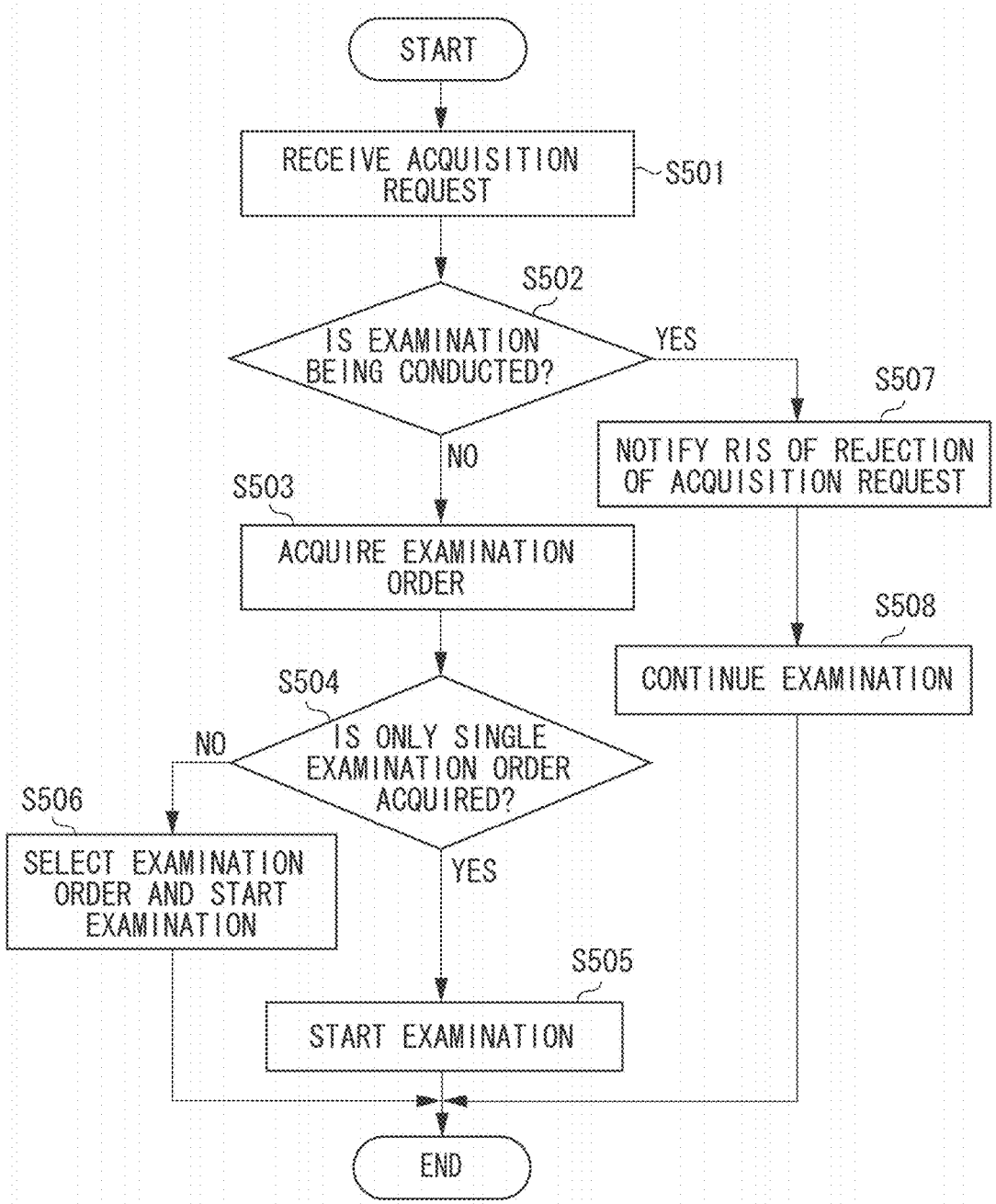

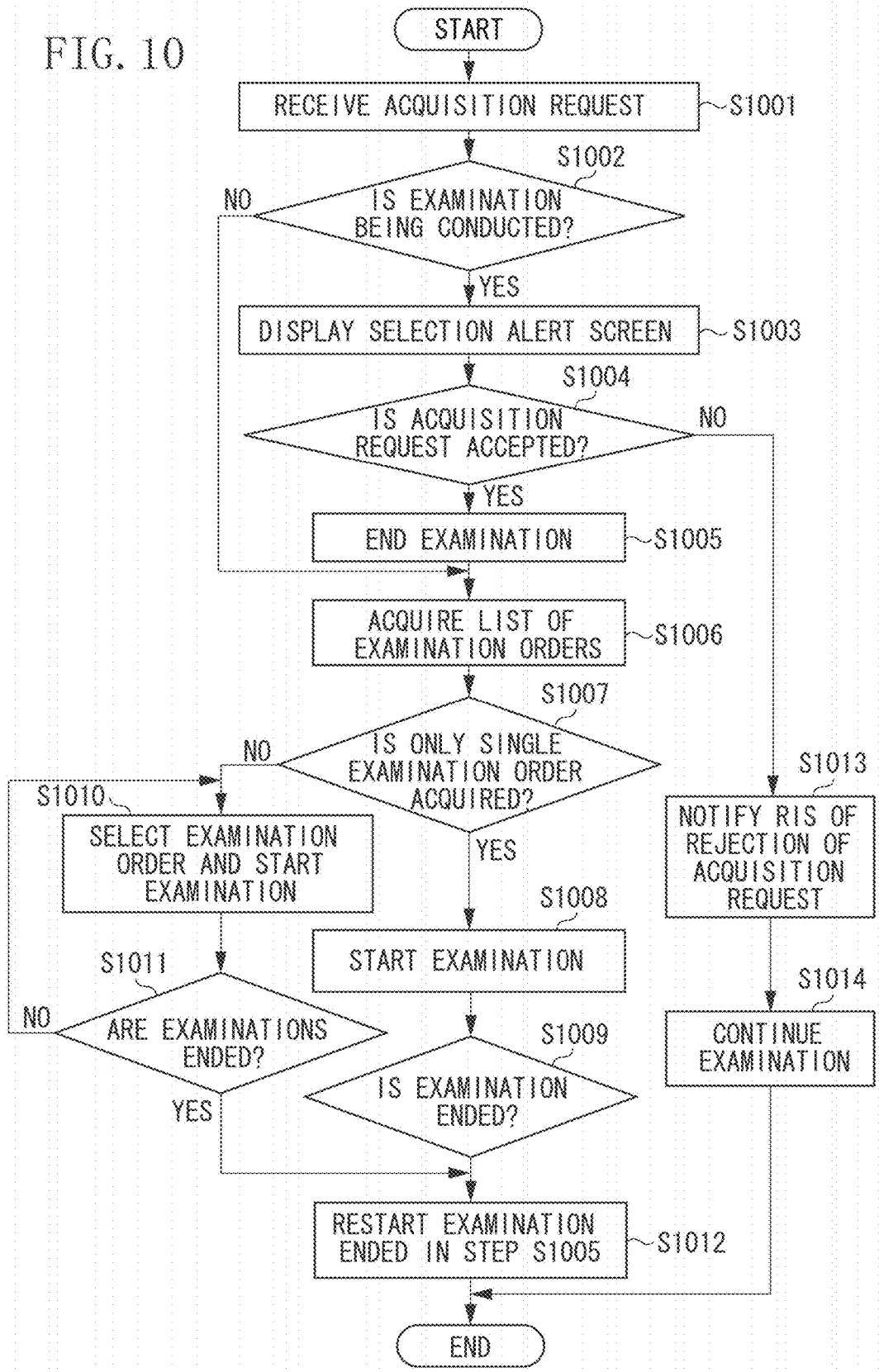

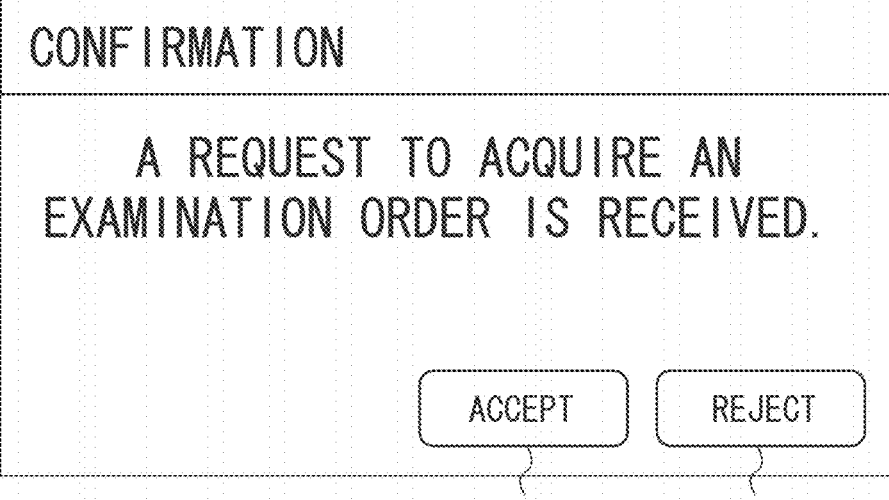

IMAGING CONTROL APPARATUS, IMAGING CONTROL SYSTEM, AND IMAGING CONTROL METHOD

BACKGROUND OF THE INVENTION

Field of the Invention

The present invention relates to an imaging control apparatus, an imaging control system, and an imaging control method especially effective in use for capturing a radiation image.

Description of the Related Art

In large-scale hospitals, an information system for a hospital that is called a Hospital Information System (HIS) may be constructed by connecting terminals (computers) in various departments in the hospital to one another via a network (refer to Japan Patent Application Laid-Open No. 2008-276288). In this case, an information system designed for each of the departments, such as a Radiology Information System (RIS), is provided for each of the departments. Such information system enables a doctor to transmit request information for an examination to another department. This request information is referred to as an examination order. The examination order contains various parameters, such as a name of a department that requests the examination, an examination item (a site to be imaged or the like if the examination is radiation imaging), personal information of a patient, and the like.

For example, when X-ray imaging is determined to be necessary, a doctor inputs request information about the examination from an HIS terminal as an examination order. The HIS terminal transmits the examination order to the RIS in a radiology department that receives a request to conduct the examination. Upon receiving the examination order, the RIS in the radiology department adds an imaging condition and the like to this examination order, and registers this examination order in a Modality Worklist Management (MWM) server. An imaging control system captures a radiation image according to the examination order received from the MWM server.

For example, one possible configuration is to set up a terminal of the RIS and a terminal of the imaging control system together in an operation room, thereby allowing an operator to operate its terminals only by moving a minimum distance. In this case, one possible operation flow is that the RIS issues a request to obtain an examination order to the imaging control system, and the imaging control system obtains the examination order upon receiving the request to obtain the examination order. This operation flow allows the operator to save time and minimize work for performing an operation on each of the terminal of the RIS and the terminal of the imaging control system to obtain the examination order.

However, if the systems are configured in this manner, it is possible that a new request to obtain an examination order may be issued when an examination has been already started. In this case, in some situations, the operator may want the imaging control system to exercise the above-described function of acquiring the examination order upon receiving the new request to obtain the examination order without requiring the operator to perform the operation, but in other situations, the operator may want the imaging control system not to exercise this function. Further, after the examination order is obtained, in some situations, the operator may want the imaging control system to carry out this examination order, and in other situations, the operator may want the imaging control system not to carry out this examination order.

SUMMARY OF THE INVENTION

According to an aspect of the present invention, an imaging control apparatus includes a display control unit configured to perform at least display control to display a screen for carrying out capturing of a radiation image based on an examination order, in response to registration of the examination order, which is an order for capturing the radiation image, and a restriction unit configured to restrict execution of the display control if information about another examination order for capturing a radiation image is displayed on the screen for carrying out the capturing of the radiation image.

According to another aspect of the present invention, an imaging control apparatus includes a display control unit configured to perform at least display control to display a screen for carrying out capturing of a radiation image based on an examination order, in response to registration of the examination order, which is an order for capturing the radiation image, and a permission unit configured to permit execution of the display control even when information about another examination order for capturing a radiation image is displayed on the screen for carrying out the capturing of the radiation image.

According to yet another aspect of the present invention, an imaging control apparatus includes a display control unit configured to perform at least display control to display a screen for carrying out capturing of a radiation image based on an examination order, in response to registration of the examination order, which is an order for capturing the radiation image, a determination unit configured to determine whether to permit execution of the display control if information about another examination order for capturing a radiation image is displayed on the screen for carrying out the capturing of the radiation image, and a control unit configured to permit display of the screen if the determination unit determines to permit the execution of the display control and restrict the display of the screen if the determination unit determines not to permit the execution of the display control.

Further features of the present invention will become apparent from the following description of exemplary embodiments with reference to the attached drawings.

BRIEF DESCRIPTION OF THE DRAWINGS

FIG. 2B illustrates the new examination input screen with examination orders displayed thereon.

FIG. 2C illustrates the new examination input screen with an examination order specified thereon.

FIG. 3 illustrates the new examination input screen with an imaging information input area displayed thereon.

FIG. 4A illustrates an imaging screen in an initial state.

FIG. 4B illustrates the imaging screen with an X-ray image displayed thereon.

FIG. 5 is a flowchart illustrating a first example of an operation of an X-ray imaging control apparatus.

FIG. 10 is a flowchart illustrating a fourth example of an operation of the X-ray imaging control apparatus.

FIG. 11 illustrates a selection alert screen.

DESCRIPTION OF THE EMBODIMENTS

Various exemplary embodiments, features, and aspects of the invention will be described in detail below with reference to the drawings.

Figure 1:
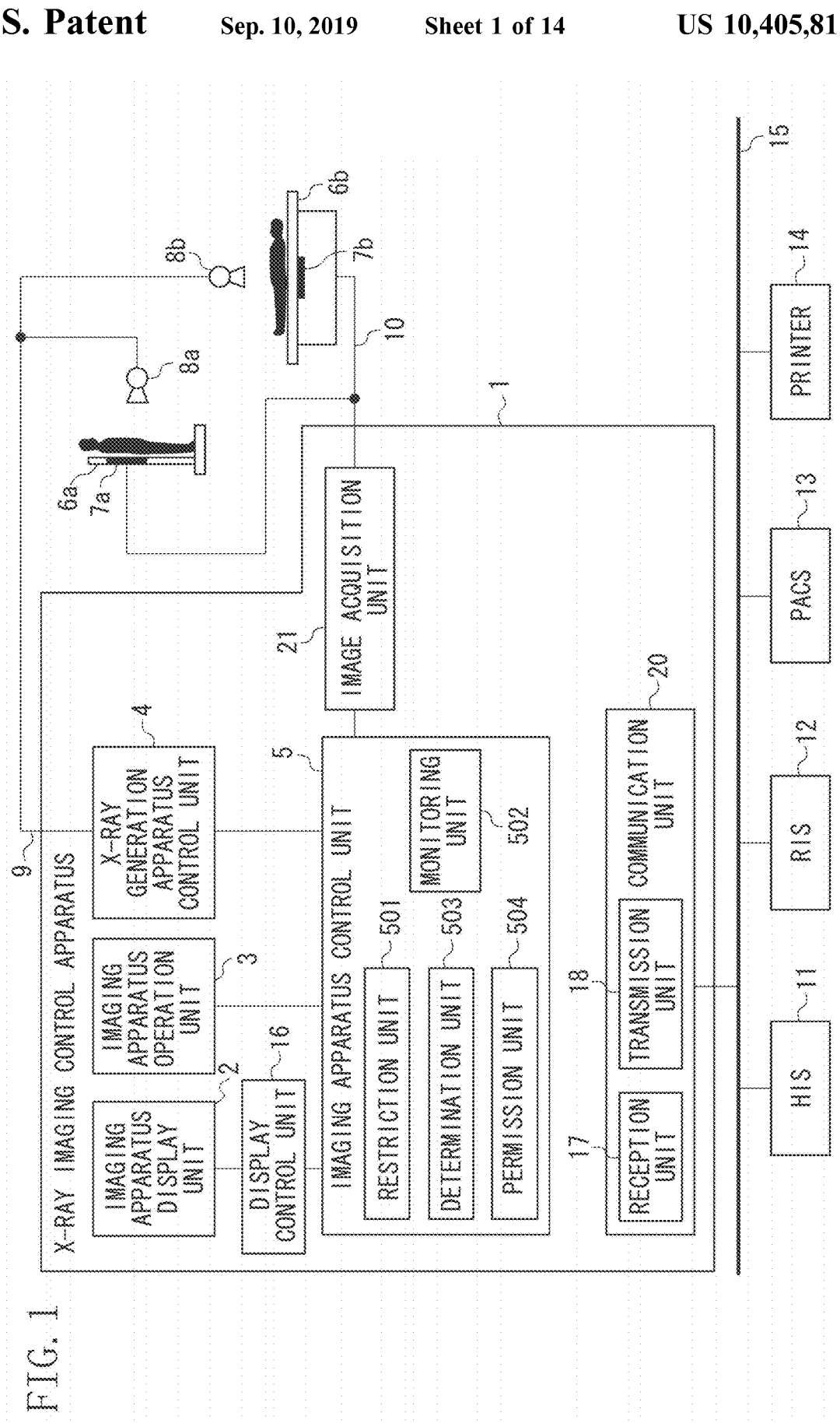
FIG. 1 illustrates a configuration of an imaging control system.

First, a first exemplary embodiment will be described. FIG. 1 illustrates an example of a configuration of an imaging control system. The present exemplary embodiment will be described based on an example in which a radiation is an X-ray. The imaging control system includes an X-ray imaging control apparatus 1 (modality), an HIS (an information system for a hospital) 11, an RIS (an information system in a radiology department) 12, a Picture Archiving and Communication System (PACS) (an image server) 13, and a printer 14. Further, the imaging control system includes imaging platforms 6a and 6b, X-ray detectors 7a and 7b, and X-ray generation units 8a and 8b. The present exemplary embodiment will be described assuming that at least the X-ray imaging control apparatus 1 and the RIS 12 are located in a same imaging room. However, the X-ray imaging control apparatus 1 and the RIS 12 do not necessarily have to be located in a same imaging room.

The HIS (Hospital Information System) 11 is a system for managing a progress of radiation imaging. The HIS 11 includes an HIS terminal. Further, the HIS 11 may include a server that manages accounting information.

When X-ray imaging is determined to be necessary, a doctor inputs request information about the examination into the HIS terminal. The HIS terminal transmits the request information about the examination to the RIS (Radiology Information System) 12 in the radiology department that receives a request to conduct the examination. This request information is referred to as an examination order. This examination order contains a name of a department that requests the examination, an examination item, personal information of a subject (a patient), and the like. Examples of the examination item include one or more site(s) or body parts of the subject to be imaged. Examples of the personal information of the subject (patient) include a name of the patient, an identification (ID) number, date of birth, age and sex category of the patient to be imaged.

Upon receiving the examination order, the RIS 12 (an RIS terminal) in the radiology department adds an imaging condition and the like to this examination order, and registers this examination order. Further, the RIS 12 transmits this examination order with the imaging condition and the like added thereto to the X-ray imaging control apparatus 1 in response to an inquiry from the X-ray imaging control apparatus 1. The X-ray imaging control apparatus 1 carries out X-ray imaging according to the received examination order. The X-ray imaging control apparatus 1 adds the examination order to a captured image. The X-ray imaging control apparatus 1 transfers the image with the examination order added thereto to the PACS (Picture Archiving and Communication System) 13, and/or outputs the image with the examination order added thereto to the printer 14. Further, the X-ray imaging control apparatus 11 transfers execution information about the examination to the HIS 11. The execution information transferred to the HIS 11 is used for accounting processing after the examination, in addition to management of a progress of the examination.

Information processing apparatuses in these respective systems are connected to one another via a network 15 realized by, for example, a local area network (LAN) or a wide area network (WAN). These information processing apparatuses each include one or more computer(s). The computer includes, for example, a main control unit such as a central processing unit (CPU), and a storage unit such as a read only memory (ROM) and a random access memory (RAM). Further, the computer may include, for example, a communication unit such as a network card, and an input/output unit such as a keyboard and pointing device (mouse) and/or a touchscreen, and a display panel (or monitor). These constituent units of the information processing apparatus are connected to one another via a bus or the like, and are controlled by the main control unit executing a program stored in the storage unit.

The present exemplary embodiment will be described based on an example in which the RIS 12 adds an imaging condition to the examination order received from the HIS terminal, and registers this examination order in the RIS 12 itself. However, the RIS 12 may register the examination order in an external apparatus instead of (or in addition to) the RIS 12. For example, upon receiving the examination order, the RIS 12 may add the imaging condition (or other imaging parameter) to the examination order, and register this examination order in a MWM (Modality Worklist Management) server. In this case, the X-ray imaging control apparatus 1 obtains the examination order registered in the MWM server (not shown). However, even in this case, a request to obtain the examination order, which will be described below, is issued from the RIS 12.

The X-ray imaging control apparatus 1 is one example of an imaging control apparatus, and includes an imaging apparatus display unit 2, an imaging apparatus operation unit 3, an X-ray generation apparatus control unit 4, an imaging apparatus control unit 5, a display control unit 16, a communication unit 20 including a reception unit 17 and a transmission unit 18, and an image acquisition unit 21. The display control unit 16 may include at least a processor to receive image data or an imaging condition, to process image data, and to output the processed image data and the received imaging condition to the imaging apparatus display unit 2. In another embodiment the display control unit 16 may include a graphic processing unit (GPU), including a connector for connecting the imaging apparatus display unit 2 by a cable, for outputting the data from the GPU to the imaging apparatus display unit 2. The reception unit 17 and the transmission unit 18 may be integrated as an antenna and an integrated circuit for controlling receipt and a transmission of signals between the X-ray imaging control apparatus 1 the apparatuses connecting to the network 15.

The X-ray generation apparatus control unit 4 is connected to the X-ray generation units 8a and 8b via a cable 9. The X-ray generation apparatus control unit 4 includes at least one processor for controlling emission of an X-ray by the X-ray generation units 8a and 8b. The X-ray generation units 8a and 8b each function as a radiation generation unit. The X-ray generation units 8a and 8b each include, for example, an X-ray tube, and emits X-ray radiation toward a subject (for example, a specific site or body part of a patient).

The imaging apparatus display unit 2 is realized by, for example, a liquid crystal display (LCD), and displays various kinds of information for observation of an operator (a radiographic technician or a doctor). An image is displayed on the imaging apparatus display unit 2 according to control by the display control unit 16. The imaging apparatus operation unit 3 includes, for example, a pointing device (mouse) and an operation button, and inputs various kinds of instructions issued from the operator into the X-ray imaging control apparatus 1. The imaging apparatus display unit 2 and the imaging apparatus operation unit 3 may be realized by a touch panel integrally including these units.

The X-ray imaging control apparatus 1 is connected to the X-ray detectors 7a and 7b via a cable 10. Power, an image signal, a control signal, and the like are transmitted and received between the X-ray imaging control apparatus 1 and the X-ray detectors 7a and 7b via the cable 10. The X-ray detectors 7a and 7b each function as a detection unit that detects the X ray radiation transmitted through the subject, and obtains an X-ray image (a radiation image) based on this subject. In other words, the X-ray generation units 8a and 8b and the X-ray detectors 7a and 7b operate in cooperation with each other, which realizes an X-ray imaging unit. The X-ray detectors 7a and 7b are set up on the imaging platform 6a for upright radiography and the imaging platform 6b for recumbent radiography, respectively.

The reception unit 17 of the communication unit 20 receives a request to obtain an examination order, one or more examination order(s), and the like from the RIS 12. As described above, the examination order contains a name of a department that requests the examination, an examination item, personal data of a subject (a patient), and the like.

The imaging apparatus control unit 5 comprehensively controls processing in the X-ray imaging control apparatus 1. The imaging apparatus control unit 5, including at least one processor, functions as an instruction unit that instructs the X-ray imaging control apparatus 1 to start X-ray imaging corresponding to at least one examination order among examination orders received from the RIS 12. The imaging apparatus control unit 5 instructs the X-ray imaging control apparatus 1 to start X-ray imaging upon receiving, for example, an input operation that the operator performs on the imaging apparatus operation unit 3 to place an examination order. Alternatively, the imaging apparatus control unit 5 may select an examination order to be carried out, and instruct the X-ray imaging control apparatus 1 to start X-ray imaging based on the selected examination order.

In one embodiment, the X-ray imaging apparatus control unit 5 may include a restriction unit 501, a monitoring unit 502, determination unit 503, and a determination unit 504. Each of the units may include one processor. In another embodiment, some of the units or all of the units may be integrated as one processor to function as each of the units. The restriction unit 501 may be configured to restrict execution of a specific display control. The display control is to display a screen for carrying out capturing of a radiation image based on an examination order, according to registration of the examination order, which is an order about the capturing of the radiation image. The restriction is executed if information about another examination order for capturing a radiation image is displayed on the screen for carrying out the capturing of the radiation image.

The monitoring unit 502 may be configured to monitor a file which is created, deleted, or has an attribute to be changed when the examination order is registered in an external apparatus. The determination unit 503 may be configured to determine whether to permit execution of the display control, if information about another examination order for capturing a radiation image is displayed on the screen for carrying out the capturing of the radiation image. The permission unit 504 may be configured to permit execution of the display control, even when information about another examination order for capturing a radiation image is displayed on the screen for carrying out the capturing of the radiation image.

In another embodiment of the present invention, the imaging control apparatus control unit 5 and, at least one of the X-ray generation apparatus control unit 4, the display control unit 16, and the integrated circuit of the communication unit 20 may be integrated as one processor to function as each of the units.

In response to this instruction to start the imaging, the transmission unit 18 transmits information indicating that the X-ray imaging based on the examination order has been started to the HIS 11. Upon receiving this information, the HIS 11 changes a status about this examination order into a status indicating that the examination has been started. After that, when all of X-ray imaging operations corresponding to this examination order are completed, and the operator does an input for confirming completion of the examination order via the imaging apparatus operation unit 3, the transmission unit 28 transmits information indicating that the X-ray imaging according to this examination order is completed, to the HIS 11. Upon receiving this information, the HIS 11 changes the status about this examination order into a status indicating that the examination is completed.

Communication used in acquisition of an examination order is performed according to a protocol defined by Digital Imaging and Communication in Medicine (DICOM). Further, a pull type implementation method is defined for an imaging apparatus worklist inquiry (Query Modality Worklist) transaction according to the Integrating the Healthcare Enterprise (IHE) technical framework. When an examination order is obtained by the pull type method, the X-ray imaging control apparatus 1 operates as a client, and inquires about an examination order to an information system (the RIS 12 or the MWM server) based on an operator's operation performed on the X-ray imaging control apparatus 1. Then, the examination order is downloaded from this information system into the X-ray imaging control apparatus 1.

On the other hand, for example, if the RIS 12 and the X-ray imaging control apparatus 1 are disposed side by side in the same imaging room, in one possible configuration, an examination order may be obtained by a push type method. When an examination order is obtained by the push type method, the X-ray imaging control apparatus 1 is configured to receive a request to obtain an examination order from the RIS 12 with use of a special protocol therefor. Then, the X-ray imaging control apparatus 1 inquires of the information system (the RIS 12 or the MWM server) about the examination order specified by the request to obtain the examination order. Then, the examination order is downloaded from the information system into the X-ray imaging control apparatus 1. By configuring the system in this manner, the operator is released from the necessity of performing operations for acquiring the examination order, on both the RIS 12 and the X-ray imaging control apparatus 1.

A request to obtain an examination order may contain a search condition for searching for the examination order. This search condition is used when the X-ray imaging control apparatus 1 obtains the examination order from the information system. However, a request to obtain an examination order does not necessarily have to contain the search condition for searching for the examination order as long as the request to obtain the examination order contains information for specifying the examination order to be obtained.

In the present exemplary embodiment, the X-ray imaging control apparatus 1 can obtain an examination order from the information system by both the above-described pull type method and push type method, and carry out X-ray imaging based on the obtained examination order. In addition, the X-ray imaging control apparatus 1 according to the present exemplary embodiment can manually input an examination order based on an operator's operation performed on the X-ray imaging control apparatus 1 without performing communication with the information system, and also carry out X-ray imaging based on the input examination order. In the following description, such a method will be referred to as a manual method.

Now, an example of a flow of processing in the imaging control system illustrated in FIG. 1 when an X-ray image is captured according to a flow of an examination will be described.

Figure 2A:
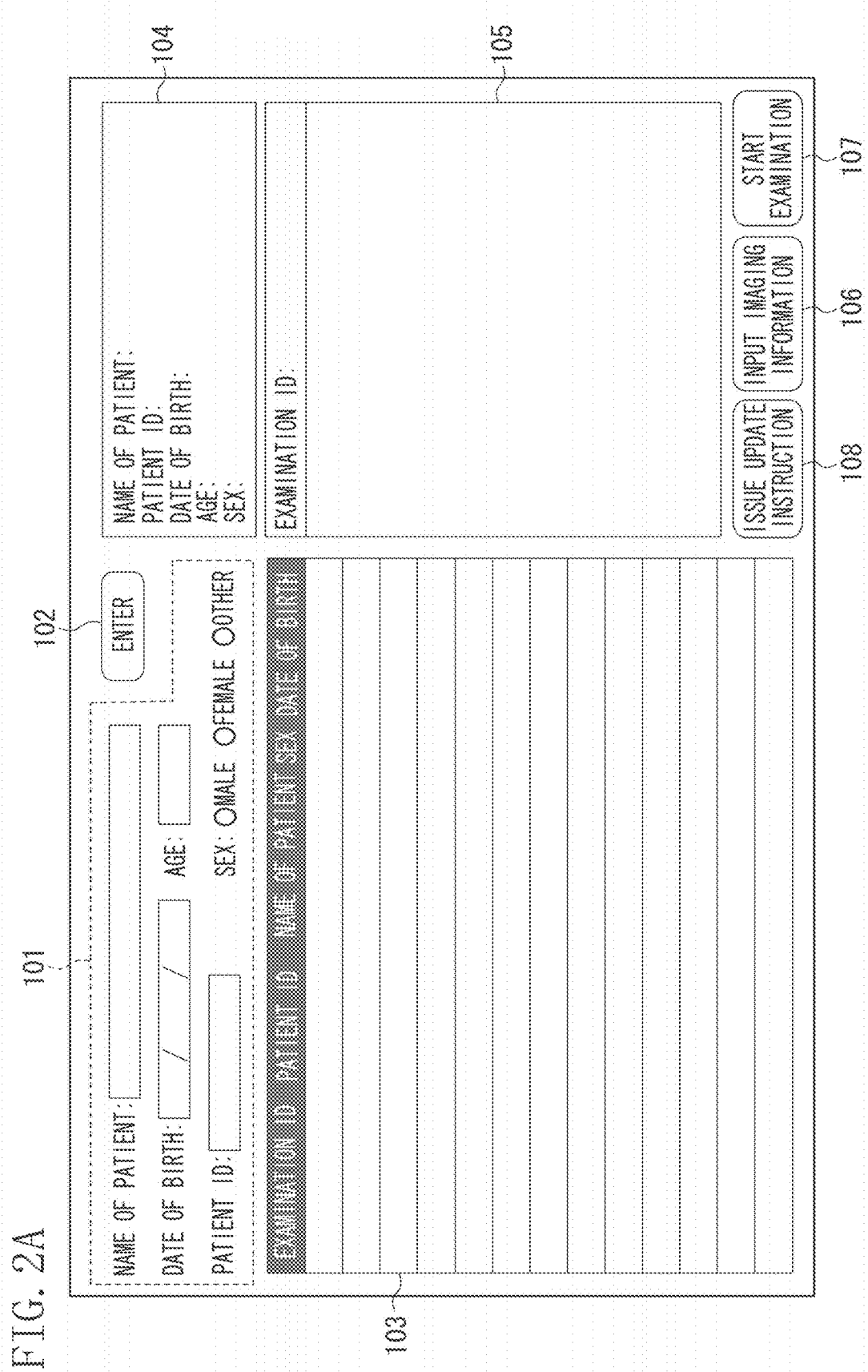
FIG. 2A illustrates a new examination input screen in an initial state.

First, the imaging apparatus display unit 2 displays a new examination input screen illustrated in FIG. 2A under the control of the display control unit 16. FIG. 2A illustrates the new examination input screen in an initial state. The new examination input screen includes a patient information input area 101, a patient information enter button 102, a requested examination list 103, a patient information display area 104, an imaging information display area 105, an imaging information input button 106, an examination start button 107, and an update instruction button 108.

Input is entered into the patient information input area 101 and the patient information enter button 102 when an examination order is obtained by the manual method. Personal data of a subject (a patient) is input (displayed) into the patient information input area 101 based on a content of an operator's operation performed on the imaging apparatus operation unit 3. After that, the operator presses the patient information enter button 102, when determining the subject's (patient's) personal data input (displayed) in the patient information input area 101. When the button 102 is pressed, the subject's (patient's) personal data input (displayed) in the patient information input area 101 when the patient information enter button 102 is pressed is displayed in the patient information display area 104.

An examination ID is displayed in the imaging information display area 105, and an imaging method corresponding to the examination ID is displayed in an area immediately below the examination ID.

In a case where an examination order is input by the manual method, the operator presses the imaging information input button 106. When the button 106 is pressed, an imaging information input area 110 is displayed on the new examination input screen as illustrated in FIG. 3. When the operator selects any one or more button(s) among imaging method buttons displayed in the imaging information input area 110, the selected imaging method button(s) is (or are) displayed in the imaging information display area 105. The imaging method button is a button for selecting the imaging method. In the present example, the imaging method button is a button for selecting a site to be imaged and a sensor for imaging the site (the X-ray detector 7a or 7b). The example illustrated in FIG. 3 indicates that a chest front view button 109a and a chest lateral view button 109b are selected.

When an examination order is obtained by the pull type method, the operator presses the update instruction button 108. When the button 108 is pressed, the transmission unit 18 inquires of the RIS 12 about an examination order. The reception unit 17 receives examination orders transmitted from the RIS 12 in response to this inquiry. A list of these examination orders is displayed in the requested examination list 103 (refer to FIG. 2B). When the operator selects any one examination order from the list of examination orders displayed in the requested examination list 103, subject's (patient's) personal data (a patient ID, a name of a patient, a date of birth, and the like) contained in the selected examination order is displayed in the patient information display area 104.

When an examination order is obtained by the push type method, the following operation is performed. First, after the RIS 12 receives an examination order from the HIS 11 and registers the examination order to thereby place the examination order into a state obtainable by the X-ray imaging control apparatus 1, the RIS 12 transmits a request to obtain the examination order to the X-ray imaging control apparatus 1.

Upon receiving the request to obtain the examination order via the reception unit 17, the imaging apparatus control unit 5 inquires of the RIS 12 about the examination order via the transmission unit 18. The reception unit 17 receives the examination order transmitted in response to this inquiry from the RIS 12. A list of examination orders received in this manner is displayed in the requested examination list 103 (refer to FIG. 2B). When the operator selects any one examination order from the list of examination orders displayed in the request examination list 103, subject's (patient's) personal data (a patient ID, a name of a patient, a date of birth, and the like) contained in the selected examination order is displayed in the patient information display area 104.

As described above, the examination ID is displayed in the imaging information display area 105. When the examination order is obtained by the pull type method or the push type method, imaging information corresponding to this examination ID is automatically displayed in the area immediately below the examination ID. The imaging information is contained in the examination order transmitted from the RIS 12 as described above. In the example illustrated in FIG. 2C, the chest front view button 109a and the chest lateral view button 109b are displayed in the imaging information display area 105 as the imaging method buttons corresponding to the imaging information. As described above, the operator can also further add an imaging method by pressing the imaging information input button 106 to display the imaging information input area 110 as illustrated in FIG. 3.

In any of the push type method, the pull type method, and the manual method, the operator presses the examination start button 107 after confirming the patient information and the imaging information obtained in the above-described manner. By this pressing, the examination to be conducted is determined. Further, in the pull type method and the push type method, when the X-ray imaging control apparatus 1 does not have to prompt the operator to select an examination order, for example, when only a single examination order is obtained as a result of the inquiry about the examination order, the operator's operation can be reduced by automatically selecting the examination order and pressing the examination start button 107. However, even when only a single examination order is obtained as a result of the inquiry about the examination order, the X-ray imaging control apparatus 1 may prompt the operator to press the examination start button 107 in a similar manner to the operation when there are two or more examination orders.

According to the pressing of the examination start button 107, the imaging apparatus display unit 2 changes the new examination input screen illustrated in FIG. 2C to an imaging screen illustrated in FIG. 4A. The imaging screen is a screen used at the time of imaging.

The imaging screen basically includes similar display areas to the new examination input screen described with reference to FIGS. 2A to 2C. On the imaging screen, a captured image display area 111 is displayed in an area where the patient information input area 101, the patient information enter button 102, and the request examination list 103 were displayed on the new examination input screen. Because imaging is not carried out yet at this stage, no X-ray image is displayed in the captured image display area 111. Further, a message area 112 is displayed above the patient information display area 104.

Further, an image processing setting area 113 is displayed immediately below the imaging information display area 105. Further, an examination end button 114 is displayed in an area where the examination start button 107 were displayed on the new examination input screen.

When the imaging screen is displayed, the imaging method button 109a that was located at an uppermost position in the imaging information display area 105 on the new examination input screen is put into a selected state as default. According thereto, the imaging apparatus control unit 5 transmits an imaging condition (an X-ray tube voltage, an X-ray tube current, an irradiation time period, and the like) set corresponding to this imaging method button (the imaging method), to the X-ray generation apparatus control unit 4. Upon receiving the imaging condition, the X-ray generation apparatus control unit 4 controls the X-ray detector 7a or 7b according to the imaging condition to make preparations for imaging. When preparations are made, the X-ray imaging control apparatus shifts to an imaging-enabled state. At this time, a "READY message", which indicates that the X-ray imaging control apparatus 1 is in the imaging-enabled state, is displayed in the message area 112.

Subsequently, the operator confirms the imaging method, and makes a setting for imaging and positions the patient. Upon completion of a series of preparations for imaging, the operator presses an X-ray emission switch (not illustrated) after confirming that the X-ray imaging control apparatus 1 is in the imaging-enabled state by referring to the message area 112. Upon pressing of this button, the X-ray generation unit 8a or 8b emits an X-ray toward the subject (a specific site of the patient) under the control of the X-ray generation apparatus control unit 4. The X-ray detector 7a or 7b detects the X-ray transmitted through this subject. In this manner, an X-ray image is captured.

After the imaging is completed, the imaging apparatus control unit 5 obtains the captured X-ray image from the X-ray detector 7a or 7b via the image acquisition unit 21. Further, the imaging apparatus control unit 5 performs image processing on this obtained X-ray image based on a predetermined image processing condition. The predetermined image processing condition is determined in advance corresponding to, for example, the imaging method.

After the image processing is completed, as illustrated in FIG. 4B, the imaging apparatus display unit 2 displays this X-ray image processed by the image processing in the captured image display area 111. For example, if the operator wants to change a contrast or the like of this X-ray image, the operator operates a button for the contrast, a luminance, or the like prepared in the image processing setting area 113. By this operation, the operator can perform additional image processing on this X-ray image displayed in the captured image display area 111. When the operator presses the imaging method button 109b for the imaging that is not carried out yet, the imaging condition and the image processing condition of this X-ray image are stored, and next imaging by the imaging method button 109b (the imaging method) is started.

The operator repeats the above-described procedure to carry out the imaging by all of the imaging method buttons 109a and 109b (the imagine methods) in the imaging information display area 105. After completion of the imaging by all of the imaging methods, the operator presses the examination end button 114. By this pressing, a series of examinations is ended, and the X-ray imaging control apparatus 1 displays the new examination input screen again.

Further, the X-ray imaging control apparatus 1 outputs the captured X-ray image, examination information (the imaging method and the like), the patient information (the subject's (patient's) personal data and the like), and the like to at least any one of, for example, the PACS 13, the printer 14, and a storage medium in the X-ray imaging control apparatus 1. This captured X-ray image and the patient information are stored in association with each other in the PACS 13, the storage medium in the X-ray imaging control apparatus 1, or the like.

It is possible that a request to obtain an examination order may be issued from the RIS 12, after the examination order is obtained by the above-described push type method, pull type method, or manual method, and the examination is started according to the obtained examination order in the above-described manner.

In such a system capable of issuing a request to obtain an examination order, it is possible that the RIS 12 issues a request to obtain an examination order after an end operation is performed on the X-ray imaging control apparatus 1.

However, this system is not a system including only a single system and in addition, this end operation is an operation that does not exist in a normal flow of repeatedly conducting an examination in an order as planned. Therefore, this solution ends up forcing the operator to perform an unfamiliar operation, which raises a possibility of the operator failing to perform the predetermined end operation and skipping the end operation.

If the end operation is skipped, even if a request to obtain an examination order is issued from the RIS 12, an examination according to a new examination order is not started because the X-ray imaging control apparatus 1 is still maintained in a status of carrying out imaging of a previous examination. Further, if the X-ray imaging control apparatus 1 accepts a request to obtain an examination order from the RIS 12, for example, operator's negligence of confirmation of patient/examination information at the time of imaging may result in inconsistency between a patient indicated by the examination order and an actually imaged patient, posing a risk of occurrence of a patient mix-up by mistake.

Therefore, according to the present exemplary embodiment, the X-ray imaging control apparatus 1 prioritizes an examination order according to which an examination has been already started over an examination order for which an acquisition request is newly issued, and the imaging apparatus control unit 5 rejects the request to obtain the examination order from the RIS 12 during a time period from a start of the examination to an end of the examination. In this case, the X-ray imaging control apparatus 1 does not comply with the request to obtain the examination order, and does not inquire of the RIS 12 about the examination order.

FIG. 5 is a flowchart illustrating an example of an operation of the X-ray imaging control apparatus 1 when an examination order (or examination orders) is (or are) received from the RIS 12.

In step S501, the imaging apparatus control unit 5 receives a request to obtain an examination order (or examination orders) via the reception unit 17.

Subsequently, in step S502, the imaging apparatus control unit 5 determines whether an examination is in progress. In the present exemplary embodiment, a flowchart will be described based on an example in which a time period since the examination start button 107 is pressed until the examination end button 114 is pressed corresponds to a time period during which an examination is in progress in any of the push type method, the pull type method, and the manual method.

If a result of this determination indicates that no examination is in progress (NO in step S502), the processing proceeds to step S503. In step S503, the imaging apparatus control unit 5 obtains the examination order(s) from the RIS 12 via the reception unit 17.

Subsequently, in step S504, the imaging apparatus control unit 5 determines whether only a single examination order has been obtained in step S503. If a result of this determination indicates that only a single examination order has been obtained (YES in step S504), the processing proceeds to step S505. In step S505, the imaging apparatus control unit 5 automatically activates the examination start button 107, and instructs the X-ray imaging control apparatus 1 to start an examination.

In this case, the imaging apparatus control unit 5 instructs the display control unit 16 to display subject's personal data contained in this examination order in the patient information display area 104 on the imaging screen illustrated in FIG. 4A. Further, the imaging apparatus control unit 5 instructs the display control unit 16 to display an imaging button corresponding to imaging information contained in this examination order in the imaging information display area 105 on the imaging screen illustrated in FIG. 4A. In this state, an X-ray image is not displayed in the captured image display area 111. Further, the imaging apparatus control unit 5 instructs the display control unit 6 to display the "READY message", which indicates that the X-ray imaging control apparatus 1 is in the imaging-enabled state, in the message area 112 on the imaging screen illustrated in FIG. 4A. After that, the examination is conducted in a manner described above with reference to FIG. 4B. Then, the processing according to the flowchart of FIG. 5 is ended.

On the other hand, if the imaging apparatus control unit 5 determines in step S504 that more than one examination orders have been obtained (there is a plurality of examination orders) (NO in step S504), the processing proceeds to step S506. In step S506, the imaging apparatus control unit 5 instructs the display control unit 16 to display a list of the plurality of examination orders in the requested examination list 103 on the new examination input screen, as illustrated in FIG. 2B.

Then, when any of the plurality of examination orders is selected by the operator as illustrated in FIG. 2C, the imaging apparatus control unit 5 instructs the display control unit 16 to display subject's personal data contained in this selected examination order in the patient information display area 104.

Further, the imaging apparatus control unit 5 instructs the display control unit 16 to display an imaging button corresponding to imaging information contained in the selected examination order in the imaging information display area 105. Then, the imaging apparatus control unit 5 instructs the X-ray imaging control apparatus 1 to start an examination when the examination start button 107 is pressed by the operator. After that, the examination is conducted in a manner described above with reference to FIGS. 4A and 4B. Then, the processing according to the flowchart of FIG. 5 is ended.

On the other hand, if the imaging apparatus control unit 5 determines that an examination is in progress in step S502 (YES in step S502), the processing proceeds to step S507. In step S507, the imaging apparatus control unit 5 notifies the RIS 12 that the X-ray imaging control apparatus 1 rejects the request to obtain the examination order(s) via the transmission unit 18. In this case, the X-ray imaging control apparatus 1 does not obtain the examination order(s) for which the acquisition request is issued from the RIS 12.

Then, in step S508, the X-ray imaging control apparatus 1 continues the ongoing examination. Upon an end of the examination, the processing according to the flowchart of FIG. 5 is ended.

Thus, according to the present exemplary embodiment, if the X-ray imaging control apparatus 1 receives a request to obtain an examination order from the RIS 12 during the time period from a start of an examination to an end of the examination, the X-ray imaging control apparatus 1 notifies the RIS 12 that the restriction unit 501 of the X-ray imaging control apparatus 1 rejects acquisition of the examination order, and does not receive the examination order. Therefore, displays of the new examination input screen and the imaging screen with respect to this examination order are restricted by the function of the restriction unit 501. Accordingly, the present exemplary embodiment can reduce the risk of occurrence of a patient mix-up by mistake (inconsistency between a patient specified by the examination order and an actually imaged patient) due to an operator's error in judgment following an interruption of a new examination order into an examination order according to which an examination is in progress.

The present exemplary embodiment has been described based on the example in which the X-ray imaging control apparatus 1 determines that a request to obtain an examination order is issued upon receiving the request to obtain the examination from the RIS 12. However, the X-ray imaging control apparatus 1 does not necessarily have to determine that a request to obtain an examination order is issued upon receiving the request to obtain the examination.

For example, this determination can be also realized by sharing a specific file between the RIS 12 and the X-ray imaging control apparatus 1. In a case where the system is configured in this manner, for example, the RIS 12 creates an acquisition request file in a specific folder. The monitoring unit in the X-ray imaging control apparatus 1 monitors a file in this folder, and determines that a request to obtain an examination order is issued upon detecting that the acquisition request file is created by the RIS 12. Alternatively, the X-ray imaging control apparatus 1 may be configured to determine that a request to obtain an examination order is issued upon detecting that the RIS 12 changes a filename of a specific file in this folder to another specific filename. Further alternatively, the X-ray imaging control apparatus 1 may be configured to determine that a request to obtain an examination order is issued upon detecting that the RIS 12 deletes a specific file in this folder.

Further, to reject a request to obtain an examination order in the case where the system is configured in the above-described manner, for example, the X-ray imaging control apparatus 1 prohibits creation of the file into this folder, deletion of the file from this folder, or a change of an attribute of the specific file in this folder during the time period from a start of an examination to an end of the examination. By prohibiting the above processing, the X-ray imaging control apparatus 1 is prevented from detecting a new request to obtain an examination order during the examination. Further, the RIS 12 can recognize that the request to obtain the examination order has been rejected when creation of the acquisition request file, deletion of the file, or a change of the attribute have failed.

Further, the present exemplary embodiment has been described based on the example in which the time period since the examination start button 107 is pressed until the examination end button 114 is pressed corresponds to the time period during which an examination is in progress in any of the push type method, the pull type method, and the manual method. However, a time period since a subject (a patient) to be examined is specified until the examination end button 114 is pressed may be treated as the time period during which an examination is in progress.

For example, when an examination order is obtained by the push type method or the pull type method, a time period since a list of examination orders is displayed in the requested examination list 103 on the new examination input screen until the examination end button 114 is pressed may be treated as the time period during which an examination is in progress. Alternatively, a time period since an examination order is selected in the requested examination list 103 on the new examination input screen for the first time until the examination end button 114 is pressed may be treated as the time period during which an examination is in progress.

Further, as described above, when an examination order is obtained by the push type method or the pull type method, and only a single examination order is obtained, the X-ray imaging control apparatus 1 can display the imaging screen (FIG. 4A and the like) without displaying the new examination input screen (FIG. 2A and the like). In this case, a time period since subject's personal data contained in this examination order is displayed in the patient information display area 104 on the imaging screen until the examination end button 114 is pressed may be treated as the time period during which an examination is in progress.

Further, when an examination order is obtained by the manual method, a time period since the patient information enter button 102 is pressed until the examination end button 114 is pressed may be treated as the time period during which an examination is in progress.

Further, when an examination order is obtained by the push type method, the X-ray imaging control apparatus 1 may display the new examination input screen in the initial state in response to reception of a request to obtain an examination order, as one example of a screen for carrying out capturing of an X-ray image based on this examination order. Further, based on acquisition of examination orders transmitted from the RIS 12 in response to an inquiry about examination orders, and registration of the examination orders with the X-ray imaging control apparatus 1 itself, the X-ray imaging control apparatus 1 may display a list of these examination orders in the requested examination list 103. In this case, the X-ray imaging control apparatus 1 may display the list of examination orders in the requested examination list 103 after displaying the new examination input screen in the initial state, or may display the new examination input screen with the list of examination orders displayed in the requested examination list 103 without displaying the new examination input screen in the initial state.

Further, functions of the apparatuses included in the imaging control system, such as the X-ray imaging control apparatus 1 and the RIS 12, may be distributed to a plurality of apparatuses (the plurality of apparatuses may be located inside Japan or may be located outside Japan). For example, a new examination input screen generated by another apparatus communicably connected to the X-ray imaging control apparatus 1 may be transmitted to the X-ray imaging control apparatus 1, and the X-ray imaging control apparatus 1 may display this new examination input screen.

Next, a second exemplary embodiment will be described. The first exemplary embodiment has been described based on the example in which, if the X-ray imaging control apparatus 1 receives a request to obtain an examination order from the RIS 12 during execution of an examination, the X-ray imaging control apparatus 1 does not receive this examination order. On the other hand, according to the present exemplary embodiment, if the X-ray imaging control apparatus 1 receives a request to obtain an examination order from the RIS 12 during the time period from a start of an examination to an end of the examination, the X-ray imaging control apparatus 1 receives and suspends this examination order, and conducts an examination according to the received examination order when the ongoing examination is ended. Thus, the present exemplary embodiment is mainly different from the first exemplary embodiment in a part of the processing performed when a request to obtain an examination order is received from the RIS 12 during execution of an examination. Therefore, in the following description of the present exemplary embodiment, similar elements to the first exemplary embodiment will not be described in detail while, for example, identifying them with the same reference numerals as those used in FIGS. 1 to 5.

Figure 6:
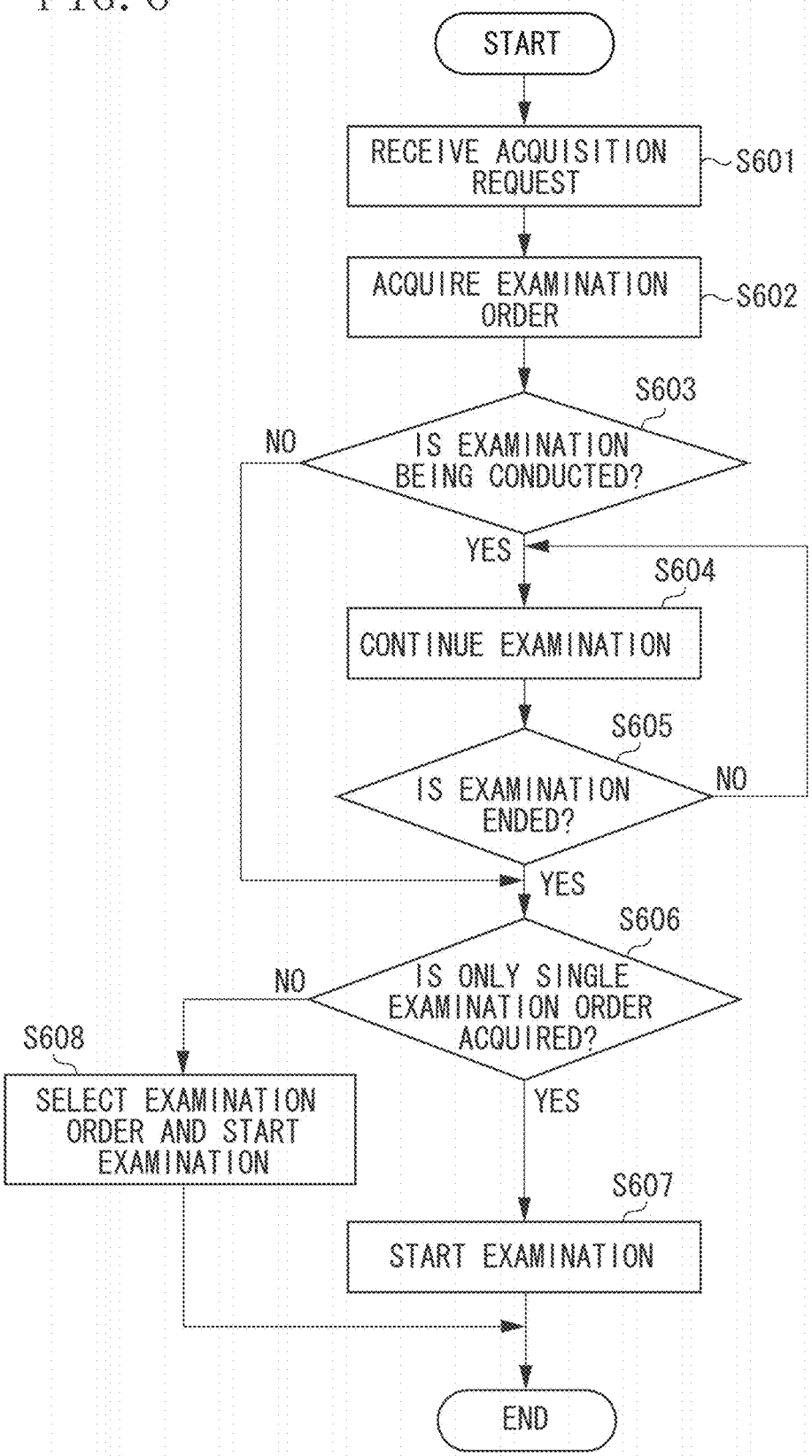
FIG. 6 is a flowchart illustrating a second example of an operation of the X-ray imaging control apparatus.

FIG. 6 is a flowchart illustrating an example of an operation of the X-ray imaging control apparatus 1 when an examination order (or examination orders) is (or are) received from the RIS 12.

In step S601, the imaging apparatus control unit 5 receives a request to obtain an examination order (or examination orders) via the reception unit 17.

Subsequently, in step S602, the imaging apparatus control unit 5 obtains the examination order(s) from the RIS 12 via the reception unit 17.

Subsequently, in step S603, the imaging apparatus control unit 5 determines whether an examination is in progress. The imaging apparatus control unit 5 determines whether an examination is in progress by the method described in the first exemplary embodiment.

If a result of this determination indicates that no examination is in progress (NO in step S603), the processing proceeds to step S606, which will be described below, while skipping steps S604 and 605.

On the other hand, if an examination is in progress (YES in step S603), the processing proceeds to step S604. In step S604, the X-ray imaging control apparatus 1 continues the ongoing examination.

Subsequently, in step S605, the imaging apparatus control unit 5 determines whether the ongoing examination is ended. More specifically, in the present exemplary embodiment, the imaging apparatus control unit 5 determines that the ongoing examination is ended when it is detected that the examination end button 114 is pressed. If a result of this determination indicates that the ongoing examination is not ended yet (NO in step S605), the processing returns to step S604, and the processes of steps S604 and S605 are repeated until the ongoing examination is ended. Then, when the ongoing examination is ended (YES in step S605), the processing proceeds to step S606.

In step S606, the imaging apparatus control unit 5 determines whether only a single examination order has been obtained in step S602. If a result of this determination indicates that only a single examination has been obtained (YES in step S606), the processing proceeds to step S607. In step S607, the X-ray imaging control apparatus 1 starts an examination according to this single examination order. The process of step S607 is similar to, for example, the process of step S505 illustrated in FIG. 5, therefore, a detailed description thereof is omitted here. Then, the processing according to the flowchart of FIG. 6 is ended.

On the other hand, if the imaging apparatus control unit 5 determines in step S606 that more than one examination orders have been obtained (there is a plurality of examination orders) (NO in step S606), the processing proceeds to step S608. In step S608, the X-ray imaging control apparatus 1 starts an examination according to an examination order selected by the operator among the plurality of examination orders. The process of step S608 is similar to, for example, the process of step S506 illustrated in FIG. 5, therefore, a detailed description thereof is omitted here. Then, the processing according to the flowchart of FIG. 6 is ended.

The present exemplary embodiment configured in this manner can also obtain a similar effect to the effect described in the first exemplary embodiment. Further, the modification examples described in the first exemplary embodiment can be also employed in the present exemplary embodiment.

Next, a third exemplary embodiment will be described. The first and second exemplary embodiments have been described based on the example in which, if the X-ray imaging control apparatus 1 receives a request to obtain an examination order from the RIS 12 during execution of an examination, the X-ray imaging control apparatus 1 prioritizes the ongoing examination over an examination according to this examination, order to continue the ongoing examination. On the other hand, there are cases where the examination according to the examination order by which the acquisition request is received should be prioritized over the ongoing examination, for example, a case that the examination order by which the acquisition request is issued from the RIS 12 is an emergency examination order.

Therefore, according to the present exemplary embodiment, if the X-ray imaging control apparatus 1 receives a request to obtain an examination order from the RIS 12 during the time period from a start of an examination to an end of the examination, the X-ray imaging control apparatus 1 prioritizes an examination according to this examination order over the ongoing examination, to start the examination according to this examination order. Thus, the present exemplary embodiment is different from the first and second exemplary embodiments mainly in a part of the processing performed when a request to obtain an examination order is received from the RIS 12 during the time period from a start of an examination to an end of the examination. Therefore, in the following description of the present exemplary embodiment, similar elements to the first and second exemplary embodiments will not be described in detail while, for example, identifying them with the same reference numerals as those used in FIGS. 1 to 6.

Figure 7:
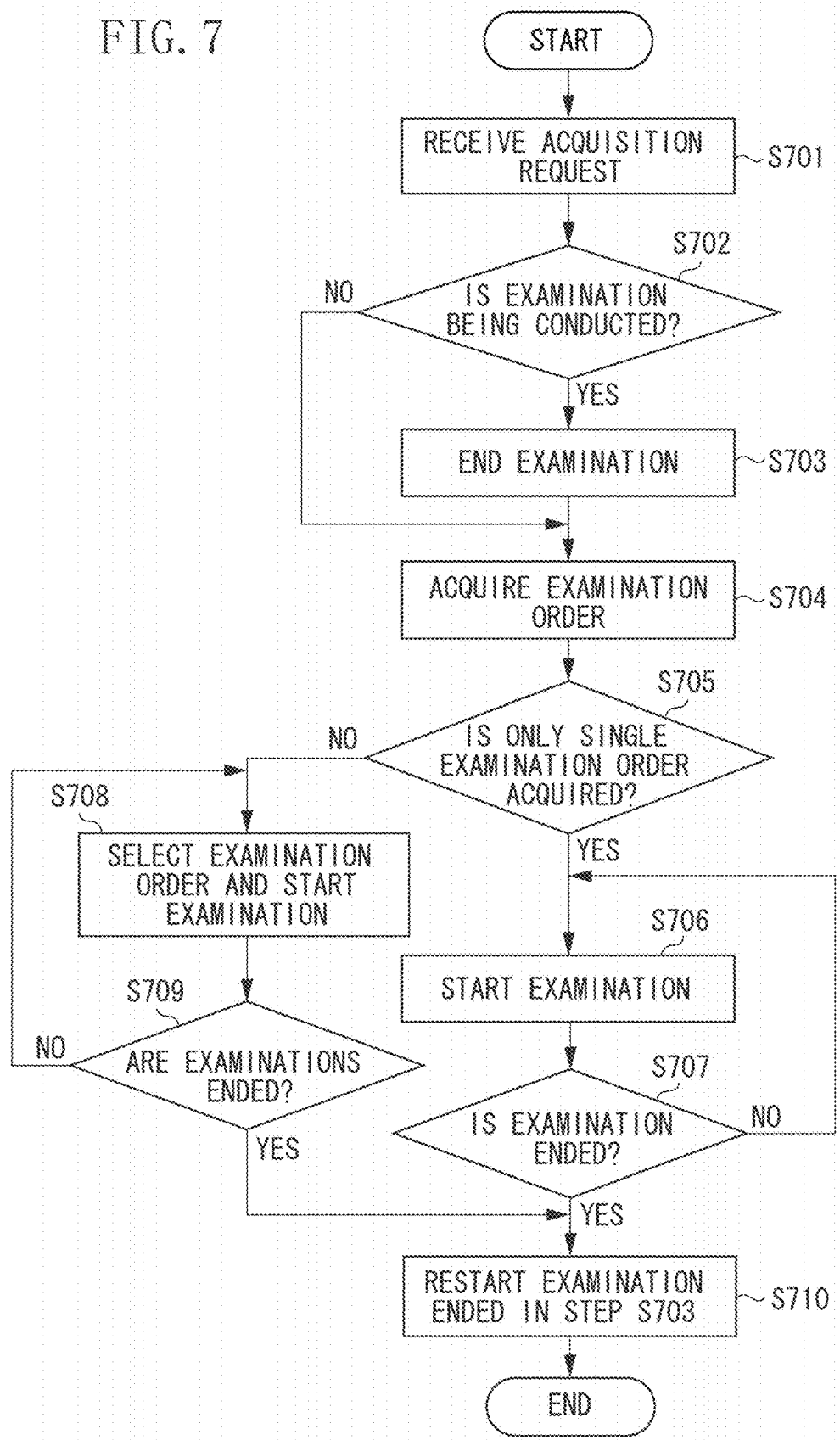
FIG. 7 is a flowchart illustrating a third example of an operation of the X-ray imaging control apparatus.

FIG. 7 is a flowchart illustrating an example of an operation of the X-ray imaging control apparatus 1 when an examination order (or examination orders) is (or are) received from the RIS 12.

In step S701, the imaging apparatus control unit 5 receives a request to obtain an examination order (or examination orders) via the reception unit 17.

Subsequently, in step S702, the imaging apparatus control unit 5 determines whether an examination is in progress. The imaging apparatus control unit 5 determines whether an examination is in progress by the method described in the first exemplary embodiment.

If a result of this determination indicates that no examination is in progress (NO in step S702), the processing proceeds to step S704, which will be described below, by skipping step S703.

On the other hand, if an examination is in progress (YES in step S702), the processing proceeds to step S703. In step S703, the X-ray imaging control apparatus 1 terminates the ongoing examination. For example, if the imaging screen illustrated in FIG. 4A is displayed, the X-ray imaging control apparatus 1 clears this imaging screen. Then, the processing proceeds to step S704.

In step S704, the imaging apparatus control unit 5 obtains the examination order(s) from the RIS 12 via the reception unit 17.

Subsequently, in step S705, the imaging apparatus control unit 5 determines whether only a single examination order has been obtained in step S704. If a result of this determination indicates that only a single examination order has been obtained (YES in step S705), the processing proceeds to step S706. In step S706, the X-ray imaging control apparatus 1 starts an examination according to this single examination order. The process of step S706 is similar to, for example, the process of step S505 illustrated in FIG. 5, therefore, a detailed description thereof is omitted here.

Subsequently, in step S707, the imaging apparatus control unit 5 determines whether the examination according to the examination order obtained in step S704 is ended. More specifically, in the present exemplary embodiment, the imaging apparatus control unit 5 determines that the examination according to the examination order obtained in step S704 is ended when it is detected that the examination end button 114 is pressed. If a result of this determination indicates that the examination according to the examination order obtained in step S704 is not ended (NO in step S707), the processing returns to step S706. Then, the processes of steps S706 and S707 are repeated until this examination is ended. Then, when the examination according to the examination order obtained in step S704 (YES in step S707) is ended, the processing proceeds to step S710, which will be described below.

If the imaging apparatus control unit 5 determines in step S705 that more than one examination orders have been obtained (there is a plurality of examination orders) (NO in step S705), the processing proceeds to step S708. In step S708, the X-ray imaging control apparatus 1 starts an examination according to an examination order selected by the operator among the plurality of examination orders.

The process of step S708 is similar to, for example, the process of step S506 illustrated in FIG. 5, therefore, a detailed description thereof is omitted here.

Subsequently, in step S709, the imaging apparatus control unit 5 determines whether examinations according to all of the examination orders obtained in step S704 are ended. The imaging apparatus control unit 5 makes this determination of step S709 by the same method as the determination method used in the above-described step S707. If a result of this determination indicates that the examinations according to all of the examination orders obtained in step S704 are not ended yet (NO in step S709), the processing returns to step S708. Then, the processes of steps S708 and S709 are repeated until the examinations according to all of the examination orders obtained in step S704 are ended. Then, when the examinations according to all of the examination orders obtained in step S704 (YES in step S709) is ended, the processing proceeds to step S710.

In step S710, the X-ray imaging control apparatus 1 restarts the examination terminated in step S703. At this time, the X-ray imaging control apparatus 1 can display a screen which was displayed when the examination has been terminated in step S703, and restart the examination from where the examination has been terminated in step 703. Alternatively, the X-ray imaging control apparatus 1 can also restart the examination terminated in step S703 from the beginning. Then, the processing according to the flowchart of FIG. 7 is ended.

As described in the first exemplary embodiment, if an examination order according to which an examination is being carried out, is interrupted by a new examination order, it poses the risk of a patient mix-up by mistake due to an operator's error in judgment. Therefore, in the present exemplary embodiment, in step S706 or S708, the imaging apparatus control unit 5 instructs the display control unit 16 to display information indicating on the imaging screen that an X-ray image is captured by interruption imaging.

Figure 8:
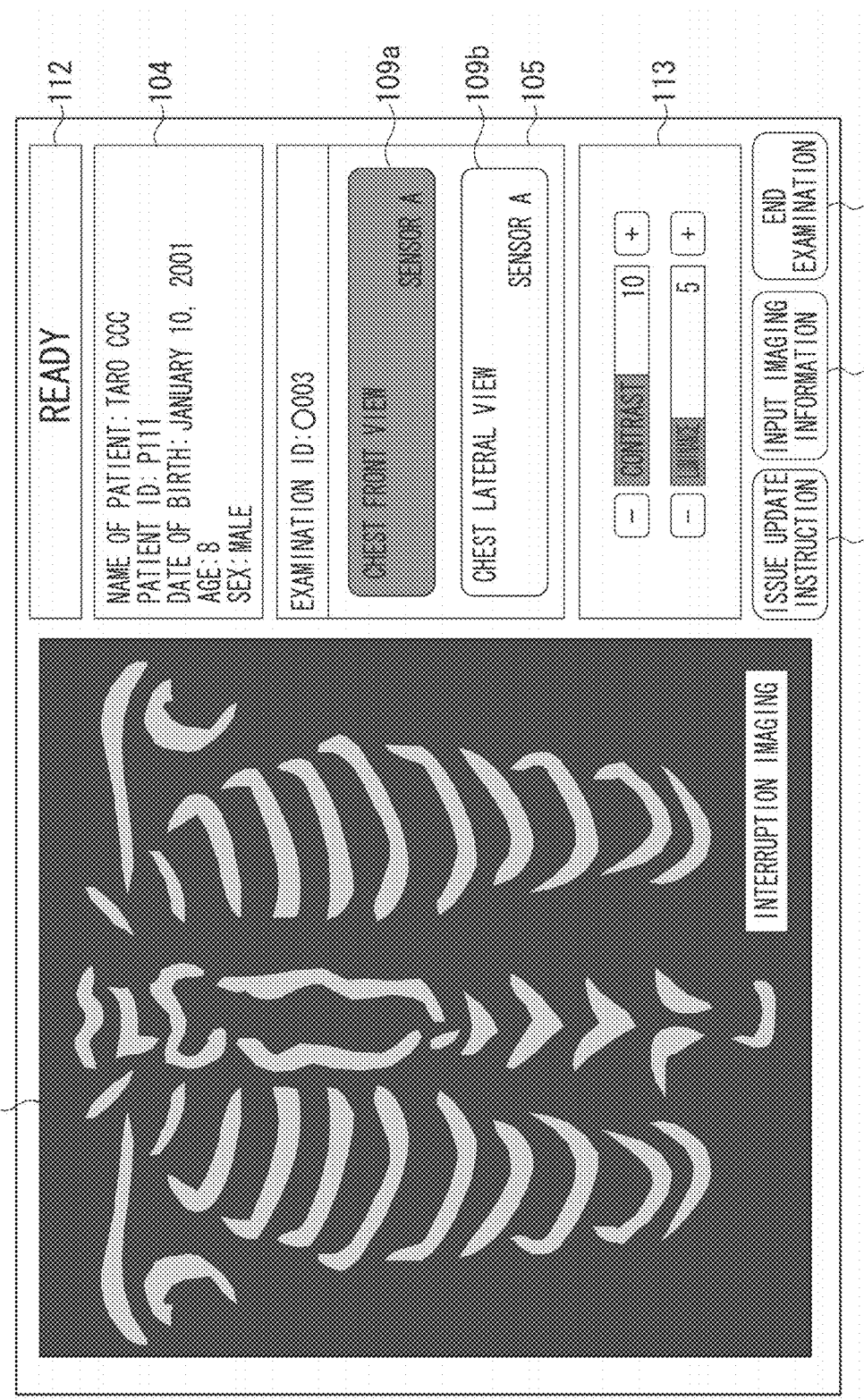
FIG. 8 illustrates a first example of the imaging screen indicating that the displayed imaging is interruption imaging.
Figure 9:
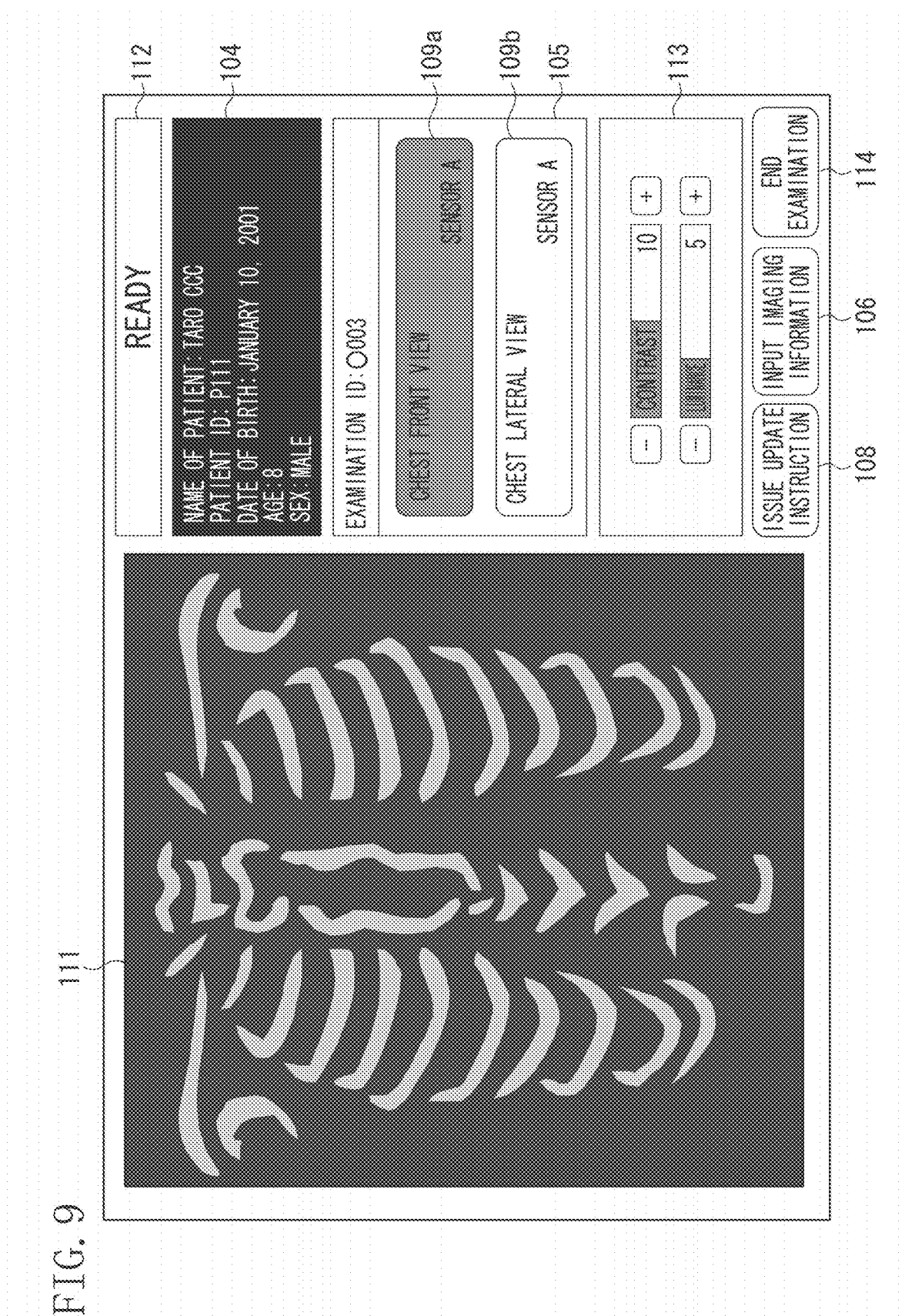
FIG. 9 illustrates a second example of the imaging screen indicating that the displayed imaging is interruption imaging.

FIGS. 8 and 9 illustrate examples of the imaging screen on which the information indicating that an X-ray image is captured by interruption imaging is displayed.

In the example illustrated in FIG. 8, a text "INTERRUPTION IMAGING" is displayed on the X-ray image (at a position in the image that does not overlap with information of the subject). In the example illustrated in FIG. 9, the patient information display area 104 on the imaging screen is displayed with the black and white reversed compared to the display of an X-ray image that is not captured by interruption imaging. As long as the information indicating that the X-ray image is captured by interruption imaging can be displayed on the imaging screen, the display does not necessarily have to be presented as illustrated in FIGS. 8 and 9.

Further, when the interruption imaging is carried out, the captured X-ray image and information indicating that this X-ray image is an image captured by the interruption imaging can be stored in association with each other. As a consequence, an indication that this X-ray image is an image captured by the interruption imaging, and/or information notifying the operator that the patient should be confirmed is displayed together with the X-ray image, every time the X-ray image is confirmed (displayed).

In this manner, according to the present exemplary embodiment, if the X-ray imaging control apparatus 1 receives a request to obtain an examination order from the RIS 12 during the time period from a start of an examination to an end of the examination, the X-ray imaging control apparatus 1 suspends the ongoing examination. Then, the X-ray imaging control apparatus 1 permits displaying of the new examination input screen and the imaging screen with respect to the examination order, and preferentially conducts an examination according to this examination order. Therefore, even if an examination order is issued during execution of another examination, an emergency examination order can be carried out by interrupting the ongoing examination.

The present exemplary embodiment has been described based on the example in which the X-ray imaging control apparatus 1 restarts the terminated examination, but the X-ray imaging control apparatus 1 may be configured not to restart the terminated examination (not to perform step S710 illustrated in FIG. 7).

In addition thereto, the modification examples described in the first and second exemplary embodiments can be also employed in the present exemplary embodiment.

Next, a fourth exemplary embodiment will be described. According to the first and second exemplary embodiments, if the X-ray imaging control apparatus 1 receives a request to obtain an examination order from the RIS 12 during execution of an examination, the X-ray imaging control apparatus 1 prioritizes the ongoing examination over an examination according to this examination order, to continue the ongoing examination. On the other hand, according to the third exemplary embodiment, if the X-ray imaging control apparatus 1 receives a request to obtain an examination order from the RIS 12 during execution of an examination, the X-ray imaging control apparatus 1 prioritizes an examination according to this examination order over the ongoing examination, to start the examination according to this examination order. In this manner, according to the first to third exemplary embodiments, the X-ray imaging control apparatus 1 unconditionally determines which should be prioritized, the examination according to the examination order or the ongoing examination.

However, in some cases, whether the examination according to the examination order or the ongoing examination should be prioritized, may vary depending on the content of the examination order or the like. Therefore, according to the present exemplary embodiment, if the X-ray imaging control apparatus 1 receives a request to obtain an examination order from the RIS 12 during execution of an examination, the X-ray imaging control apparatus 1 determines whether the ongoing examination or an examination according to this examination order should be prioritized. In this manner, the present exemplary embodiment is different from the first to third exemplary embodiments mainly in a part of the processing performed when a request to obtain an examination order is received from the RIS 12 during execution of an examination. Therefore, in the following description of the present exemplary embodiment, similar elements to the first to third exemplary embodiments will not be described in detail while, for example, identifying them with the same reference numerals as those used in FIGS. 1 to 9.

FIG. 10 is a flowchart illustrating an example of an operation of the X-ray imaging control apparatus 1 when an examination order (or examination orders) is (or are) received from the RIS 12.

In step S1001, the imaging apparatus control unit 5 receives a request to obtain an examination order (or examination orders) via the reception unit 17.

Subsequently, in step S1002, the imaging apparatus control unit 5 determines whether an examination is in progress. The imaging apparatus control unit 5 determines whether an examination is in progress by the method described in the first exemplary embodiment.

If a result of this determination indicates that no examination is in progress (NO in step S1002), the processing proceeds to step S1006, which will be described below.

On the other hand, if an examination is in progress (YES in step S1002), the processing proceeds to step S1003. In step S1003, the imaging apparatus control unit 5 instructs the display control unit 16 to display a selection alert screen in the foreground.

FIG. 11 illustrates an example of the selection alert screen 1100.

In the example illustrated in FIG. 11, the selection alert screen 1100 is a dialog that makes an inquiry to the operator to confirm whether to accept the request to obtain the examination order(s). An acceptance button 1101 and a rejection button 1102 are displayed on the selection alert screen 1100.

If the operator prioritizes the examination order(s) by which the acquisition request is issued and complies with this acquisition request, the operator presses the acceptance button 1101. On the other hand, if the operator prioritizes the ongoing examination and rejects the acquisition request, the operator presses the rejection button 1102.

In step S1004, the determination unit 503 in the imaging apparatus control unit 5 determines whether to accept the request to obtain the examination order(s) based on a result of the operator's operation performed on the selection alert screen 1100. In the example illustrated in FIG. 11, if the acceptance button 1101 is pressed, the determination unit 503 in the imaging apparatus control unit 5 determines to accept the request to obtain the examination order(s) (YES in step S1004). On the other hand, if the rejection button 1102 is pressed, the determination unit 503 in the imaging apparatus control unit 5 determines not to accept (to reject) the request to obtain the examination order(s) (NO in step S1004).

If a result of this determination indicates rejection of the request to obtain the examination order(s) (NO in step S1004), the processing proceeds to step S1013, which will be described below.

On the other hand, if the result of the determination indicates acceptance of the request to obtain the examination order(s) (YES in step S1004), the permission unit 504 in the imaging apparatus control unit 5 permits execution of a display control to display a screen for carrying out capturing of a radiation image based on an examination order, in response to registration of the examination order. the processing proceeds to steps S1005 to S1008, in which the display control is going to be executed. In step S1005, the X-ray imaging control apparatus 1 terminates the ongoing examination. The process of step S1005 is similar to step S703 illustrated in FIG. 7.

Subsequently, in step S1006, the imaging apparatus control unit 5 obtains the examination order(s) from the RIS 12 via the reception unit 17. After that, the processes of steps S1007 to S1012 are performed. More specifically, the X-ray imaging control apparatus 1 conducts an examination (or examinations) according to the examination order(s) obtained in step S1006. After an end of this examination (or examinations), the X-ray imaging control apparatus 1 restarts the examination terminated in step S1005. The processes of steps S1007 to S1012 are similar to the processes of steps S705 to S710 illustrated in FIG. 7, respectively, whereby detailed descriptions of the processes of steps S1007 to S1012 are omitted.

If the imaging apparatus control unit 5 determines to reject the request to obtain the examination order(s) in step S1004 (NO in step S1004), and the processing proceeds to step S1013, the processes of steps S1013 and S1014 are performed. More specifically, the X-ray imaging control apparatus 1 notifies the RIS 12 that the X-ray imaging control apparatus 1 rejects the request to obtain the examination order(s), and continues the ongoing examination. The processes of steps S1013 and S1014 are similar to the processes of steps S507 and S508 illustrated in FIG. 5, respectively, whereby detailed descriptions of the processes of steps S1013 and S1014 are omitted.

In this manner, according to the present exemplary embodiment, if the X-ray imaging control apparatus 1 receives a request to obtain an examination order from the RIS 12 during execution of an examination, the X-ray imaging control apparatus 1 prompts the operator to determine whether the ongoing examination or an examination according to this examination order should be prioritized. Therefore, the X-ray imaging control apparatus 1 can preferentially conduct an examination that the operator determines as more prioritized between the examination order for which the acquisition request is issued, and the ongoing examination.

The present exemplary embodiment has been described based on the example in which, if the X-ray imaging control apparatus 1 rejects the request to obtain the examination order, the X-ray imaging control apparatus 1 does not receive this examination order in a similar manner to the first exemplary embodiment. However, the X-ray imaging control apparatus 1 may be configured to receive and suspend the examination order, and conduct an examination according to the examination order after an end of the ongoing examination, in a similar manner to the second exemplary embodiment. Such processing can be realized by, for example, performing the processes of steps S602 to S608 illustrated in FIG. 6 instead of the processes of steps S1013 and S1014 illustrated in FIG. 10.

Further, the present exemplary embodiment has been described based on the example in which the X-ray imaging control apparatus 1 prompts the operator to determine whether the ongoing examination or the examination according to the examination order by which the acquisition request is received should be prioritized. However, the X-ray imaging control apparatus 1 (the imaging apparatus control unit 5) may automatically determine which should be prioritized, the ongoing examination or the examination according to the examination order by which the acquisition request is received.

For example, when registering a highly emergent examination order in the RIS 12, the operator operates the RIS 12 to input information indicating its high emergency into the RIS 12. By this input, the RIS 12 registers this examination order and an emergency order flag while associating them with each other. Then, the RIS 12 transmits the emergency order flag together with a request to obtain this examination order to the X-ray imaging control apparatus 1.

If the emergency order flag is added to a request to obtain an examination order, the X-ray imaging control apparatus 1 (the imaging apparatus control unit 5) accepts this acquisition request. On the other hand, if the emergency order flag is not added to a request to obtain an examination order, the X-ray imaging control apparatus 1 (the imaging apparatus control unit 5) rejects this acquisition request. If the X-ray imaging control apparatus 1 accepts the request to obtain the examination order in this manner, the X-ray imaging control apparatus 1 terminates an ongoing examination (refer to step S1005 illustrated in FIG. 10). Therefore, in this case, it is desirable that the imaging apparatus control unit 5 instructs the display control unit 16 to display information indicating a shift to an examination to be carried out based on the emergency examination order in the foreground of the screen before the termination of the ongoing examination, and terminates the ongoing examination after displaying this information. Further, the display control unit 16 may display a screen for making an inquiry to (prompting) the operator to confirm whether to accept the shift to the examination according to the emergency examination order in the foreground, instead of only displaying the information indicating the shift to the examination according to the emergency examination order. In this case, only when the operator performs an operation for indicating acceptance of the shift to the examination to be carried out based on the emergency examination order on this screen, the X-ray imaging control apparatus 1 shifts to the examination according to the emergency examination order.

Further, the present exemplary embodiment has been described based on the example in which the X-ray imaging control apparatus 1 displays the selection alert screen 1100 to make an inquiry to the operator to confirm whether to accept a request to obtain an examination order after receiving the request to obtain the examination order. However, the X-ray imaging control apparatus 1 may be configured to cause the operator to set whether to accept a request to obtain an examination order in advance (for example, before receiving the request to obtain the examination order (before step S1001 illustrated in FIG. 10)). In a case where the X-ray imaging control apparatus 1 is configured in this manner, the process of step S1003 illustrated in FIG. 10 becomes unnecessary. Instead thereof, for example, the X-ray imaging control apparatus 1 displays a screen that allows the operator to set whether to accept a request to obtain an examination order at timing before step S1001 illustrated in FIG. 10. Then, the X-ray imaging control apparatus 1 determines whether acceptance of a request to obtain an examination order is set on this screen, instead of making the determination in step S1004. Further, the X-ray imaging control apparatus 1 may display a screen that allows the operator to set whether, when the above-described emergency order flag is added to a request to obtain an examination order, the operator accepts a shift to an examination according to this emergency examination order, at timing before step S1001 illustrated in FIG. 10. For example, if acceptance of a request to obtain an examination order is set on this screen, and the emergency order flag is added to a request to obtain an examination order, the imaging apparatus control unit 5 determines YES in step S1004. If not, the imaging apparatus control unit 5 determines NO in step S1004. Further, the X-ray imaging control apparatus 1 may have both of the setting functions with use of these screens, or may have any one of the functions. In addition thereto, the modification examples described in the first to third exemplary embodiments can be also employed for the present exemplary embodiment.

In this manner, according to the above-described exemplary embodiment, it is possible to determine whether to accept an interruption of an examination order appropriately according to a situation. Any of the above-described exemplary embodiments only indicates an example of embodiments of the present invention when the present invention is carried out, and the technical scope of the present invention should not be construed to be restricted by these exemplary embodiments. In other words, the present invention can be carried out in various kinds of forms without departing from its technical idea or its main features.

(Other Exemplary Embodiments)

The present invention can be also realized by processing including supplying a program capable of realizing one or more function(s) of the above-described exemplary embodiments to a system or an apparatus via a network or a storage medium, and causing one or more processor(s) in a computer of this system or apparatus to read out and execute the program. Further, the present invention can be also realized by a circuit (for example, an application specific integrated circuit (ASIC)) capable of realizing one or more function(s).

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not restricted to the disclosed exemplary embodiments. The scope of the following claims is to be accorded the broadest interpretation so as to encompass all such modifications and equivalent structures and functions.

This application claims the benefit of Japanese Patent Application No. 2014-066246 filed Mar. 27, 2014, which is hereby incorporated by reference herein in its entirety.

What is claimed is:

1. An imaging control apparatus comprising:
   at least one processor; and
   at least one memory storing instructions that, when executed by the at least one processor, cause the imaging control apparatus to perform operations including:
   acquiring a notification relating to an examination order, wherein the notification is sent in a case where the examination order has been registered in an external apparatus, wherein the notification includes information for specifying the examination order;
   in a case where the examination is not in progress, acquiring the examination order corresponding to the notification from the external apparatus;
   in response to acquisition of the examination order registered in the external apparatus, causing a display unit to display a screen for carrying out an examination relating to the examination order; and
   in a case where the examination is in progress, restricting acquisition of the examination order registered in the external apparatus.

2. The imaging control apparatus according to claim 1, wherein the operations further include:
   monitoring a file which is created, which is deleted, or which has an attribute to be changed when the examination order is registered in the external apparatus; and prohibiting creation of the file, deletion of the file, or a change of the attribute, in a case where the examination is in progress.

3. The imaging control apparatus according to claim 1, wherein the examination order is not received, if other examination order is determined on the screen for carrying out an examination relating to the other examination order.

4. A radiation imaging apparatus comprising:
the imaging control apparatus according to claim 1;
a radiation generation unit configured to generate a radiation based on an instruction from the imaging control apparatus; and
a detection unit configured to detect the radiation generated by the radiation generation unit.

5. An imaging control system comprising:
the imaging control apparatus according to claim 1; and
an information processing apparatus configured to issue a notification indicating that the examination order is registered in the imaging control apparatus.

6. The imaging control apparatus according to claim 1,
wherein in a case where one examination order is received, the display unit is caused to display the screen,
wherein in a case where a plurality of examination orders is received, the display unit is caused to display a list of pieces of information relating to the plurality of examination orders.

7. The imaging control apparatus according to claim 1,
wherein in a case where the examination is in progress, the external apparatus is notified that the examination order registered in the external apparatus is not to be received.

8. An imaging control method comprising:
acquiring a notification relating to an examination order, wherein the notification is sent in a case where the examination order has been registered in an external apparatus, wherein the notification includes information for specifying the examination order;
in a case where the examination is not in progress, acquiring the examination order corresponding to the notification from the external apparatus;
in response to acquisition of the examination order registered in the external apparatus, causing the display unit to display a screen for carrying out an examination relating to the acquired examination order; and
in a case where the examination is in progress, restricting acquisition of the examination order registered in the external apparatus.

9. The imaging control method according to claim 8, further comprising:
registering the examination order; and
issuing a notification indicating that the examination order is registered.

10. An imaging control system comprising:
at least one processor; and
at least one memory storing instructions that, when executed by the at least one processor, cause the imaging control apparatus to perform operations including:
acquiring a notification relating to an examination order, wherein the notification is sent in a case where the examination order has been registered in an external apparatus, wherein the notification includes information for specifying the examination order;
in a case where the examination is not in progress, acquiring the examination order corresponding to the notification from the external apparatus;
in response to acquisition of the examination order registered in the external apparatus, causing a display unit to display a screen for carrying out an examination relating to the acquired examination order; and
in a case where the examination is in progress, restricting acquisition of the examination order registered in the external apparatus.

\* \* \* \* \*